US009142146B2

(12) United States Patent
Merkle et al.

(10) Patent No.: US 9,142,146 B2
(45) Date of Patent: Sep. 22, 2015

(54) CRANIAL BONE SURROGATE AND METHODS OF MANUFACTURE THEREOF

(75) Inventors: Andrew C. Merkle, Gaithersburg, MD (US); Jack C. Roberts, Columbia, MD (US); Catherine M. Carneal, Silver Spring, MD (US); Jeffrey M. Paulson, Catonsville, MD (US); Matthew S. Johannes, Catonsville, MD (US); Liming M. Voo, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 507 days.

(21) Appl. No.: 13/487,492

(22) Filed: Jun. 4, 2012

(65) Prior Publication Data

US 2014/0302306 A1    Oct. 9, 2014

(51) Int. Cl.
| G09B 23/30 | (2006.01) |
| B32B 5/20 | (2006.01) |
| B32B 27/06 | (2006.01) |
| B32B 27/38 | (2006.01) |

(Continued)

(52) U.S. Cl.
CPC ............ *G09B 23/30* (2013.01); *B29C 44/1228* (2013.01); *B29C 44/326* (2013.01); *B32B 5/20* (2013.01); *B32B 27/065* (2013.01); *B32B 27/38* (2013.01); *B29K 2075/00* (2013.01); *B29K 2995/0063* (2013.01); *B29K 2995/0097* (2013.01); *B29L 2009/00* (2013.01); *B32B 2250/40* (2013.01); *B32B 2262/02* (2013.01); *B32B 2262/101* (2013.01); *B32B 2266/0278* (2013.01); *B32B 2266/06* (2013.01); *B32B 2305/022* (2013.01); *B32B 2305/07* (2013.01); *B32B 2305/22* (2013.01); *B32B 2307/54* (2013.01); *B32B 2307/558* (2013.01); *B32B 2307/72* (2013.01); *B32B 2535/00* (2013.01); *Y10T 428/249991* (2015.04)

(58) Field of Classification Search
USPC ....................................... 428/304.4
See application file for complete search history.

(56) References Cited

U.S. PATENT DOCUMENTS

| 4,451,416 A | 5/1984 | Burtscher |
| 4,691,556 A | 9/1987 | Mellander et al. |

(Continued)

FOREIGN PATENT DOCUMENTS

GB            2472423 A    *   2/2011

OTHER PUBLICATIONS

Chong, A.C.M., et al, "Fracture Toughness and Fatigue Crack Propagation Rate of Short Fiber Reinforced Epoxy Composites for Analogue Cortical Bone," J. of Biomech. Eng., vol. 129, Aug. 2007, pp. 487-493.

(Continued)

*Primary Examiner* — Hai Vo
(74) *Attorney, Agent, or Firm* — Noah J. Hayward (57) ABSTRACT

A surrogate multilayered material includes a first fiber reinforced layer; the first reinforced layer including a crosslinked polymer and fibers; a second fiber reinforced layer; the second reinforced layer including the crosslinked polymer and the fibers; a foam layer; the foam layer disposed between the first fiber reinforced layer and the second fiber reinforced layer; where opposite faces of the foam layer are in direct contact with the first fiber reinforced layer and the second fiber reinforced layer; the foam layer having a compressive strength of about 3.5 to about 4.5 MPa, when measured as per ASTM-D-1621-73, and a shear strength of 1.50 to about 2.15 MPa, when measured as per ASTM-C-273.

21 Claims, 2 Drawing Sheets

(51) Int. Cl.
  *B29C 44/12* (2006.01)
  *B29C 44/32* (2006.01)
  *B29K 75/00* (2006.01)
  *B29L 9/00* (2006.01)

(56) References Cited

U.S. PATENT DOCUMENTS

| | | | |
|---|---|---|---|
| 4,708,836 | A | 11/1987 | Gain et al. |
| 5,397,361 | A | 3/1995 | Clark |
| 5,947,918 | A | 9/1999 | Jones et al. |
| 6,206,703 | B1 | 3/2001 | O'Bannon |
| 6,691,585 | B2 | 2/2004 | Ahn |
| 6,957,961 | B1 | 10/2005 | Owens et al. |
| 7,204,165 | B1 | 4/2007 | Plaga et al. |
| 2004/0053055 | A1* | 3/2004 | Robinson et al. ............ 428/413 |
| 2006/0142407 | A1* | 6/2006 | Hollmann et al. ............ 521/172 |
| 2008/0172779 | A1 | 7/2008 | Ferguson |
| 2009/0165662 | A1* | 7/2009 | Ritchie ........................ 101/376 |
| 2009/0292198 | A1 | 11/2009 | Kleiven et al. |
| 2010/0197848 | A1* | 8/2010 | Verghese et al. ............ 524/502 |
| 2012/0164373 | A1* | 6/2012 | Spencer et al. ............... 428/116 |

OTHER PUBLICATIONS

Thali, M.J., et al., "A "skin-skull-brain model" for the biomechanical reconstruction of blunt forces to he human head," Forensic Science International 125 (2002), pp. 195-200.

Thali, M.J., et al., "The "Skin-skull-brain model": a new instrument for the study of gunshot effects," Forensic Science International 125 (202) pp. 178-189.

* cited by examiner

CRANIAL BONE SURROGATE AND METHODS OF MANUFACTURE THEREOF

STATEMENT OF GOVERNMENT INTEREST

This invention was made with Government support under contract number W911-QY-09-C-0058 awarded by the U.S. Army. The Government has certain rights in the invention.

BACKGROUND OF THE INVENTION

1. Field of the Invention

This disclosure relates to a cranial bone surrogate and to methods of manufacture thereof. In particular, this disclosure relates to a cranial bone surrogate for high speed impact simulations and to methods of manufacture thereof.

2. Description of the Related Art

The cranial bone plays an important role in protecting the brain from damage during accidents. Bone generally comprises a multilayered structure having a high stiffness compact bone and a much lower stiffness, low density, porous structure called a trabecular bone. Cranial bone, in particular, comprises a three layer structure. The inner and outer layers are called the "tables" and consist of compact bone, which has a high density and stiffness. There is a layer between the inner and outer tables, which has a much lower density, but acts as an energy absorber and it is termed the "diploe". In order to measure behavior of the cranial bone when subjected to a variety of impacts at different velocities, it is desirable to produce artificial materials (hereinafter termed a "surrogate material") that can replicate bone behavior.

It has been suggested that a conventional surrogate bone material for a femur or vertebrae might include an E-fiber-epoxy composite. However, it is not known how to manufacture such a composite. Moreover, detailed structure and/or dimensions of any such composite are not known. In addition, the femur and vertebrae have different structures from the cranial bone and are never subjected to the same magnitude of forces during an impact test.

Accordingly, there is a long-felt need to develop a surrogate material that behaves similar to bone. The surrogate material can be tested in human surrogate models in a variety of simulated impact environments. By using a surrogate material that replicates the behavior and performance of a real cranial bone in high and low speed impact tests, various measurements can be made during these tests by positioning transducers at various points on the cranial bone. These measurements cannot be made with real or live specimens. In addition, the use of a surrogate material for manufacturing the cranial bone permits the measurement and characterization of the types of fractures that a live person would undergo when subjected to similar forms of impact.

It is therefore desirable to have a surrogate material that replicates the behavior of the cranial bone and that can be mass produced to perform a variety of tests under different circumstances.

SUMMARY OF THE INVENTION

Disclosed herein is a surrogate multilayered material comprising a first fiber reinforced layer; the first reinforced layer comprising a crosslinked polymer and fibers; a second fiber reinforced layer; the second reinforced layer comprising the crosslinked polymer and the fibers; a foam layer; the foam layer disposed between the first fiber reinforced layer and the second fiber reinforced layer; where opposite faces of the foam layer are in direct contact with the first fiber reinforced layer and the second fiber reinforced layer; the foam layer having a compressive strength of about 3.5 to about 4.5 MPa, when measured as per ASTM-D-1621-73, and a shear strength of 1.50 to about 2.15 MPa, when measured as per ASTM-C-273.

Disclosed herein too is a method comprising disposing a first fiber reinforced layer on a first surface of a foam layer; disposing a second fiber reinforced layer on a second surface of the foam layer; where the first and second surfaces of the foam layer are opposedly disposed; where the first fiber reinforced layer and the second fiber reinforced layer are adhesively bonded to the foam layer; where the foam layer has a compressive strength of about 3.5 to about 4.5 MPa when measured as per ASTM-D-1621-73; and a shear strength of 1.50 to about 2.15 MPa when measured as per ASTM-C-273.

Disclosed herein too is a method of producing a surrogate multilayer material comprising extruding a first fiber reinforced layer from a first extruder; extruding a second fiber reinforced layer from a second extruder; extruding a foam layer from a third extruder; and laminating the first fiber reinforced layer, the second reinforced layer and the foam layer in a roll mill; where the foam layer has the first fiber reinforced layer and the second fiber reinforced layer disposed on opposing surfaces.

DETAILED DESCRIPTION

Disclosed herein is a surrogate multilayered material that replicates cranial bone behavior in a variety of impact tests conducted at different speeds. The multilayered material comprises a first fiber reinforced layer and a second fiber reinforced layer disposed on opposite surfaces of a polymeric foam. In an exemplary embodiment, the first fiber reinforced layer and the second fiber reinforced layer are in direct contact with the opposite surface of the polymeric foam and are bonded to the polymeric foam.

The surrogate multilayered material has a number of advantages. The surrogate multilayered material has properties that mimic those of the cranial bone under different conditions. For example, the surrogate "tables" (i.e., the first fiber reinforced layer and a second fiber reinforced layer) display a fracture toughness of about 2.5 MPa$\sqrt{m}$ in a 3-point bend test when conducted according to ASTM D 5045, and a tensile strength of 53±5 MPa when conducted according to ASTM D 628. The overall surrogate three layer material displays a bending modulus of 3±2 MPa and a bending strength of 68±6 MPa when conducted according to ASTM D 790. It can be manufactured in a batch manufacturing process or in a continuous manufacturing process. It can also be manufactured in large quantities for storage (on a shelf) under appropriate conditions and taken off the shelf for usage only when desired.

The first fiber reinforced layer and a second fiber reinforced layer used in the surrogate multilayered material comprise a crosslinked polymer and fibers. The crosslinked polymer may be partially or completely crosslinked after it is mixed with the fibers. It is usually completely crosslinked after it is molded to form a surrogate cranial bone.

Examples of polymers that can be crosslinked are epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing crosslinked polymers.

Exemplary polymers are epoxy polymers. Epoxy polymers comprise a "resin" or "compound" and the "hardener" or "activator". The resin consists of monomers or short chain polymers with an epoxide at either end. Most common epoxy resins are produced from a reaction between epichlorohydrin and bisphenol-A, though the latter may be replaced by other chemicals. The hardener generally comprises amine or polyamine monomers, for example triethylenetetramine (TETA). When the resin and the hardener are mixed together, the amine groups react with the epoxide groups to form a covalent bond. Each amine group can react with an epoxide group, so that the resulting epoxy polymer is heavily crosslinked, and is thus rigid and strong.

Exemplary epoxy resins are diglycidyl ether of bisphenol A, diomethane diglycidyl ether, 2,2-bis(4-glycidyloxyphenyl)propane, 2,2'-((1-methylethylidene)bis(4,1-phenyleneoxymethylene))bisoxirane, 2,2-bis(4-(2,3-epoxypropyloxy)phenyl)propane, 2,2-bis(4-hydroxyphenyl)propane, diglycidyl ether, 2,2-bis(p-glycidyloxyphenyl)propane, 4,4'-bis(2,3-epoxypropoxy)diphenyldimethylmethane, 4,4'-dihydroxydiphenyldimethylmethane diglycidyl ether, 4,4'-isopropylidenebis(1-(2,3-epoxypropoxy)benzene), 4,4'-isopropylidenediphenol diglycidyl ether, bis(4-glycidyloxyphenyl)dimethylmethane, bis(4-hydroxyphenyl)dimethylmethane diglycidyl ether, diglycidyl ether of bisphenol F, 2-(butoxymethyl)oxirane, the reaction product of 2-(chloromethyl)oxirane and 4-[2-(4-hydroxyphenyl)propan-2-yl]phenol also known as bisphenol A-epichlorohydrin based epoxy, modified bisphenol A-epichlorohydrin based epoxy, or the like, or a combination comprising at least one of the foregoing epoxy resins.

An exemplary epoxy is the diglycidyl ether of bisphenol F, also known as EPON 862® and having the structure shown in Formula (1):

(1)

In another exemplary embodiment, the epoxy is a modified diglycidyl ether of bisphenol F also known as a modified EPON 862® and having the structure shown in Formula (2):

(2)

where n is the number of repeat units. The epoxy of the formula (2) is produced by polymerizing bisphenol F with the EPON 862.

In yet another exemplary embodiment, the epoxy is the reaction product of 2-(chloromethyl)oxirane and 4-[2-(4-hydroxyphenyl)propan-2-yl]phenol also known as bisphenol A-epichlorohydrin based epoxy of the formula (3) below:

(3)

The epoxy of formula (3) is commercially available as EPON 815C. Other exemplary variations formula (3) that can be used in the first fiber reinforced layer and a second fiber reinforced layer are shown in the formulas (4) and (5)

(4)

(5)

A crosslinking agent is generally used to crosslink the crosslinked resin. The crosslinking agent is generally termed a hardener when used with epoxies. The hardener used in the epoxy is generally an amine. The amines may be polymeric or non-polymeric. The amines may be primary, secondary or tertiary amines. Examples of suitable amines are diethylene triamine, triethylenetetramine, tetraethylenepentamine, polyoxypropylenediamine, polyoxypropylenetriamine, aminothylpiperazine, or the like, or a combination comprising at least one of the foregoing amine hardener. An exemplary hardener is triethylene tetramine also commercially available as EPIKURE 3234® commercially available from Momentive Performance Materials Inc. Another exemplary commercially available hardener is EPIKURE 3274® commercially available from Momentive Performance Materials Inc.

The crosslinking agent is used in an amount of about 5 to about 40 wt %, specifically about 5 to about 35 wt %, based on the total weight of the matrix used in the first fiber reinforced layer and a second fiber reinforced layer.

In one embodiment, two or more crosslinking agents may be used in the preparation of the first and second reinforced layers. In one embodiment, a first and a second crosslinking agent may be used in the manufacturing of the first and the second reinforced layers. The first crosslinking agent has a lower activation temperature than the second crosslinking agent. As a result, during the processing of the reinforced layers, only the first crosslinking agent is activated after which the reinforced layers are placed on a shelf pending further usage. When the surrogate multilayered material is desired, the reinforced layers are taken off the shelf and combined with a foam at a temperature effective to bond the reinforced layers with the foam. The sandwich may then be placed in a mold and heated to a temperature and pressure effective to activate the second crosslinking agent as well as to form the multilayered material into the desired shape. The resulting multilayered material is the surrogate multilayered material having the desired properties.

The fibers used in the first fiber reinforced layer and a second fiber reinforced layer can be manufactured from a wide variety of different materials and has an aspect ratio greater than 1. As used herein, the fibers may therefore exist in the form of whiskers, needles, rods, tubes, strands, elongated platelets, lamellar platelets, ellipsoids, micro fibers, nanofibers and nanotubes, elongated fullerenes, or the like, or a combination comprising at least one of the foregoing shapes. Where such fibers exist in aggregate form, an aggregate having an aspect ratio greater than 1 will also suffice for exemplary embodiments of the present invention.

The fibers may contain an organic material, an inorganic material or a combination thereof. Organic fibers may be naturally occurring fibers or synthetic fibers. Naturally occurring organic fibers include wood flour obtained by pulverizing wood, cellulose, cotton, sisal, jute, cloth, hemp cloth, felt, and natural cellulosic fabrics such as Kraft paper, cotton paper, glass fiber containing paper, starch, cork flour, lignin, ground nut shells, corn, rice grain husks, or the like, or a combination comprising at least one of the foregoing naturally occurring organic fibers.

Synthetic organic reinforcing fibers may also be used in the first fiber reinforced layer and a second fiber reinforced layer. This includes organic polymers capable of forming fibers such as polyethylene terephthalate, polybutylene terephthalate and other polyesters, polyarylates, polyethylene, polyvinylalcohol, polytetrafluoroethylene, acrylic resins, high tenacity fibers with high thermal stability including aromatic polyamides, polyaramid fibers such as those commercially available from Du Pont de Nemours under the trade name KEVLAR®, polybenzimidazole, polyimide fibers such as those available from Dow Chemical Co. under the trade names POLYIMIDE 2080® and PBZ® fiber, polyphenylene sulfide, polyether ether ketone, polyimide, polybenzoxazole, aromatic polyimides or polyetherimides, or the like, or a combination comprising at least one of the synthetic organic reinforcing fibers may also be used.

Examples of suitable inorganic fibers, including processed mineral fibers such as those derived from blends comprising at least one of aluminum silicates, aluminum oxides, magnesium oxides, calcium sulfate hemihydrate, boron fibers, ceramic fibers such as silicon carbide, fibers from mixed oxides of aluminum, boron and silicon, or the like, or a combination comprising at least one of the foregoing inorganic fibers. Also included among fibers are single crystal fibers or "whiskers" including silicon carbide, alumina, boron carbide, iron, nickel, copper, or the like, or a combination comprising at least one of the foregoing inorganic fibers.

In an exemplary embodiment, glass fibers are used in the first fiber reinforced layer and a second fiber reinforced layer. Useful glass fibers include "E-glass," "A-glass," "C-glass," "D-glass," "R-glass," "S-glass," as well as E-glass derivatives that are fluorine-free and/or boron-free, or the like, or a combination comprising at least one of the foregoing fibers. Exemplary glass fibers are E-glass fibers.

Commercially produced glass fibers generally having nominal filament diameters of about 4.0 to about 35.0 micrometers and specifically about 9.0 to about 30.0 micrometers. The filaments are made by standard processes, e.g., by steam or air blowing, flame blowing, and mechanical pulling. Exemplary filaments for plastics reinforcement are made by mechanical pulling. Use of non-round fiber cross section is also possible. The glass fibers may be sized or unsized. Sized glass fibers are conventionally coated on at least a portion of their surfaces with a sizing composition selected for compatibility with the polymeric matrix material. The sizing composition facilitates wet-out and wet-through of the matrix material upon the fiber strands and assists in attaining desired physical properties in the composite.

In one embodiment, the fibers are treated with tetraphosphitozirconate commercially available as KZ55®, prior to being blended with the crosslinked polymer. In an embodiment, it is to be noted that the crosslinked polymer may not be crosslinked (i.e., it is uncrosslinked) at the time of mixing with the fibers. In yet another embodiment, the crosslinked polymer may be partially crosslinked at the time of mixing with the fibers.

The fibers used in the first and the second fiber reinforced layer are milled fibers having a length of about 1 millimeter to about 5 millimeters, specifically about 1.25 millimeters to about 4 millimeters, and more specifically about 1.50 millimeters to about 3 millimeters.

In general, the amount of fiber present in the first and the second fiber reinforced layer can be about 20 to about 50 wt %, specifically about 25 to about 40 wt %, and more specifically about 30 to about 35 wt %, based on the total weight of the first or the second fiber reinforced layer.

The first or second fiber reinforced layer generally has a fracture toughness of about 1 to about 20 MPa√m. An exemplary value of the fracture toughness for the first or second fiber reinforced layer is about 2 to about 10 MPa√m, when measured as per ASTM D 5045.

The first or second fiber reinforced layer generally has a tensile strength of about 40 to about 130 MPa. An exemplary value for the tensile strength for the first or second fiber reinforced layer is about 50 to about 70 MPa, when measured as per ASTM D 628.

The three layer structure generally has a bending strength of about 60 to about 150 MPa, when measured as per ASTM D 790. An exemplary value for the bending strength for the first or second fiber reinforced layer is about 50 to about 90 MPa, when measured as per ASTM D 790.

The first and the second fiber reinforced layer each have thicknesses of about 1 millimeter to about 3 millimeter, specifically about 1.7 to about 2.2 millimeters when used in the surrogate multilayered material.

The organic polymer used in the foam may be selected from a wide variety of thermoplastic resins, blend of thermoplastic resins, thermosetting resins, or blends of thermoplastic resins with thermosetting resins. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, or the like, or a combination comprising at last one of the foregoing organic polymers. Examples of the organic polymer are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, polyethylene terephthalate, polybutylene terephthalate, polyurethane, polytetrafluoroethylene, fluorinated ethylene propylene, perfluoroalkoxyethylene, polychlorotrifluoroethylene, polyvinylidene fluoride, or the like, or a combination comprising at least one of the foregoing organic polymers. An exemplary organic polymer for use as a foam between the first and the second fiber reinforced layer is polyurethane.

The foam may be a closed cell foam or an open cell foam having a compressive strength of about 3.5 to about 4.5 MPa, specifically about 3.75 to about 4.25 MPa when measured as per ASTM-D-1621-73. The foam has a tensile strength of about 2.75 to about 3.25 MPa, specifically about 2.90 to about 3.20 MPa, a shear strength of 1.50 to about 2.15 MPa when measured as per ASTM-C-273, and a flexural strength of 5.00 to about 5.50 MPa, specifically about 5.15 to about 5.35 MPa. In an exemplary embodiment, the foam is a rigid open cell foam manufactured from polyurethane.

It is desirable for the polyurethane foam to have a density of about 0.27 to about 0.32 grams per square centimeters (prior to being used in the surrogate multilayered material). The foam when used in the surrogate multilayered material has a thickness of about 3.0 to about 5.0 millimeters, specifically about 3.75 to about 4.25 millimeters. An exemplary foam is Rencast Polyurethane 6405 or a polyurethane foam obtained from US Composites. An exemplary polyurethane foam is a 16 pound density polyurethane foam, having Catalogue #FOAM 1616 which is commercially available from US composites.

The polyurethane is generally prepared by mixing a polyisocyanate package and a polyol package in a weight ratio of about 40/60 to about 60/40, and specifically in a weight ratio of about 45/55 to about 55/45. In an exemplary embodiment, the polyisocyanate package and the polyol package are mixed in a 50/50 weight ratio.

As noted above, the surrogate multilayered material may be manufactured in a batch process or in a continuous manufacturing process. In a batch process, the precursor to the crosslinked polymer (also termed the resin) is first blended with the fibers following which it is blended with the crosslinking agent (also known as the hardener) to form a curable composition. The curable composition is placed in a mold and cured at a suitable pressure and temperature for a suitable period of time. The cured panel is then cut into two pieces which form the first and the second fiber reinforced layers respectively.

The cured panels are then placed in a mold and a foam mixture is injected between the panels. The foam mixture fills the region between the two panels prior to expansion to form the foam. The foam then expands while simultaneously undergoing crosslinking to form the surrogate multilayered material. During the expansion and crosslinking the foam bonds to the first and the second fiber reinforced layers. The foam acts as the diploe in the surrogate multilayered material. Any excess foam may then be trimmed.

In one embodiment, a preformed foam may be placed between the first and the second fiber reinforced layers and the entire sandwich is subjected to compression at a suitable pressure and temperature to promote bonding between the respective fiber reinforced layers and the foam.

The surrogate multilayered material may also be manufactured in a continuous process. In the continuous process the precursors to the crosslinked polymer is first mixed with the fibers in a first device that imparts shear to the mixture to effect a uniform dispersion of the fibers in the precursor. Following this, the crosslinking agent is blended with the mixture of the precursor and the fiber in a section of the first device that lies downstream of the section where the mixing of the fiber and the precursor has previously taken place. Two layers of partially crosslinked polymer and fiber are discharged from the first device towards a roll mill.

A second device is used to produce a layer of the foam. The foam is then discharged from the second device and placed between the two layers of partially crosslinked polymer and fiber and the sandwich is then directed to a roll mill, where the sandwich is subjected to shear at an elevated temperature in the nip of the roll mill. The sandwich is compressed at a temperature and pressure effective to bond the first and second layers to the foam and also to effect the complete crosslinking of the first and second layers as well as the crosslinking of the foam.

In one embodiment, when two or more crosslinking agents having different activation temperatures are used, the first and second fiber reinforced layers are only subjected to a temperature to activate one of the crosslinking agents. Upon forming the multilayered material, it is placed on a shelf until it is desired to form a new surrogate cranial bone. At this time, the multilayered material is placed in a mold and deformed to the requisite shape. Following this deformation, the multilayered material may be elevated to the appropriate temperature to activate the second and/or third crosslinking agent, thus producing the surrogate multilayered material having the desired shape.

The first and second devices described above are ones where a combination of shear forces, extensional forces, compressive forces, ultrasonic energy, electromagnetic energy, thermal energy or combinations comprising at least one of the foregoing forces or forms of energy and is conducted in processing equipment wherein the aforementioned forces or forms of energy are exerted by a single screw, multiple screws, intermeshing co-rotating or counter rotating screws, non-intermeshing co-rotating or counter rotating screws, reciprocating screws, screws with pins, screws with screens, barrels with pins, rolls, rams, helical rotors, or combinations comprising at least one of the foregoing.

Melt blending involving the aforementioned forces may be conducted in machines such as single or multiple screw extruders, Buss kneader, Henschel, helicones, Ross mixer, Banbury, roll mills, molding machines such as injection molding machines, vacuum forming machines, blow molding machine, or the like, or combinations comprising at least one of the foregoing machines. In an exemplary embodiment, the first and the second devices are single screw extruders.

The first and the second fiber reinforced layers are coextruded from the first single screw extruder, while the foam is extruded and blown in the second single screw extruder. The first and the second fiber reinforced layers are aligned with the foam during their travel to the roll mill. The pressure exerted by the rolls of the roll mill promotes lamination of the various layers to form the surrogate multilayered material.

The surrogate multilayered material can be manufactured in three layers as detailed above or in a plurality of layers (5, 7, 9 layers and so on) where a layer of foam is disposed between alternating fiber reinforced layers. In one embodiment, an outer layer of foam may not be disposed between alternating fiber reinforced layers, especially after the total number of layers in the surrogate multilayered material exceeds three layers.

As noted above, the surrogate multilayered material closely replicates properties of the cranial bone and can therefore be used to simulate the properties of this particular bone in a variety of different impact situations. The material is also advantageous because it can be stored on a shelf for extended periods of time and formed into a desired shape only when necessary.

Exemplary embodiments of the present invention are further illustrated by the following non-limiting examples.

EXAMPLE 1

This example was conducted to demonstrate a method for manufacturing the surrogate multilayered material. It was also conducted to demonstrate that the surrogate multilayered material has properties that are proximate to the properties displayed by the cranial bone.

Aluminum molds having dimensions of 6 1/2 inches×13 3/4 inches×0.0080 inches (2 millimeters) were injected with an epoxy mixture comprising EPON 815C®/EPIKURE 3234®. Milled glass fibers having an average length of 1/16 inch were mixed into some of the epoxy samples that were placed in the aluminum molds. The properties of the outer fibrous layers (i.e., the tables) and the surrogate multilayered material is shown in the Table 1 below.

The filled molds were then cured at 90 pounds per square inch (0.62 MPa) for four hours. The cured epoxy panels were removed from the molds and trimmed into 15 centimeters×15 centimeters squares.

Figure 1:
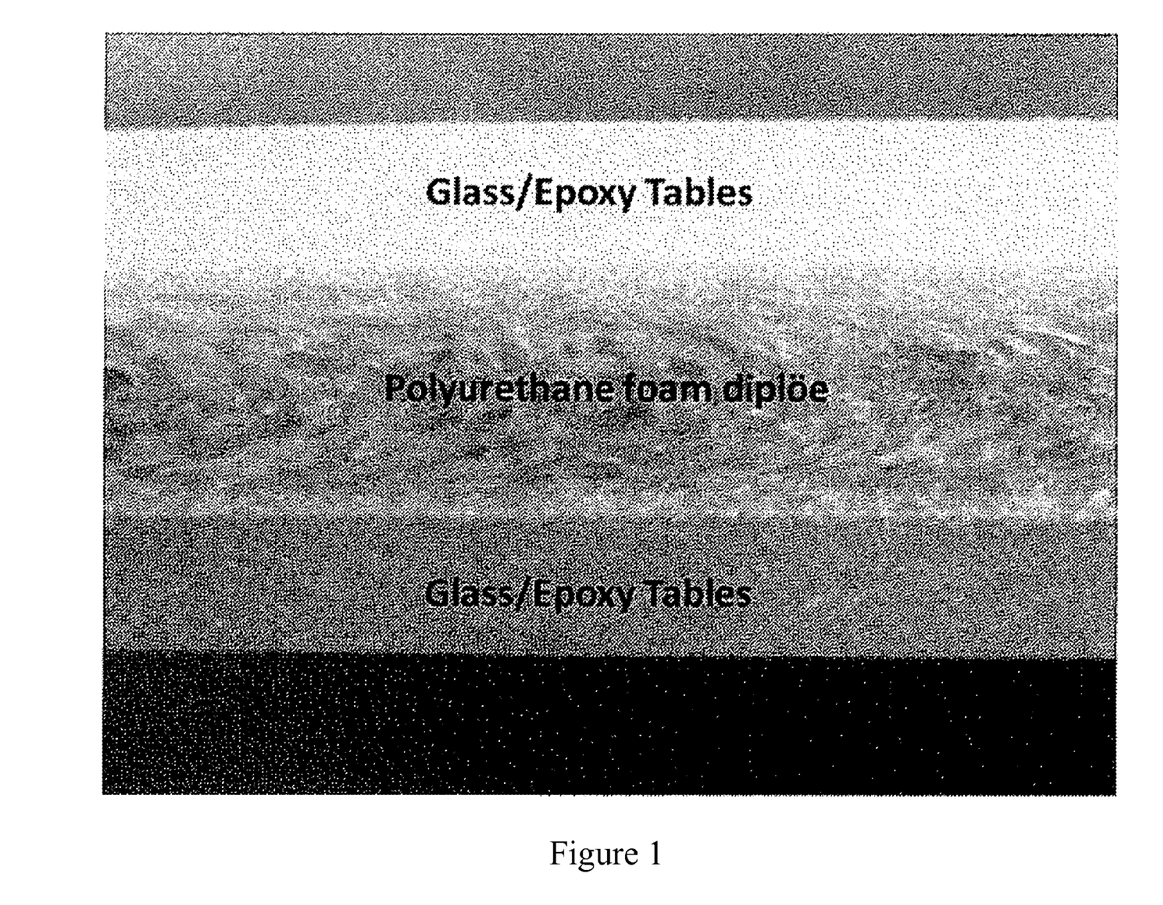
FIG. 1 depicts a photograph of the cross section of a surrogate multilayered material according to an exemplary embodiment.

The urethane material (obtained by US composites) having a free rise density of 16 pounds per cubic feet (0.25 grams per cubic centimeters) was used as the diploe. Two epoxy panels were placed in the aluminum molds and the urethane foam mixture was poured in between the two epoxy panels. The urethane pour foam mixture fills the panel core completely while still in liquid form. This is shown in photograph in the FIG. 1. The FIG. 1 depicts a photograph of the cross section of the surrogate multilayered material and shows the polyurethane diploe disposed between the first and second fiber reinforced layer. The curing of the polyurethane foam is an exothermic reaction during which the polyurethane foam bonds to the epoxy panels to form the surrogate multilayered material. The surrogate was then removed from the molds and the excess material was trimmed.

Figure 2:
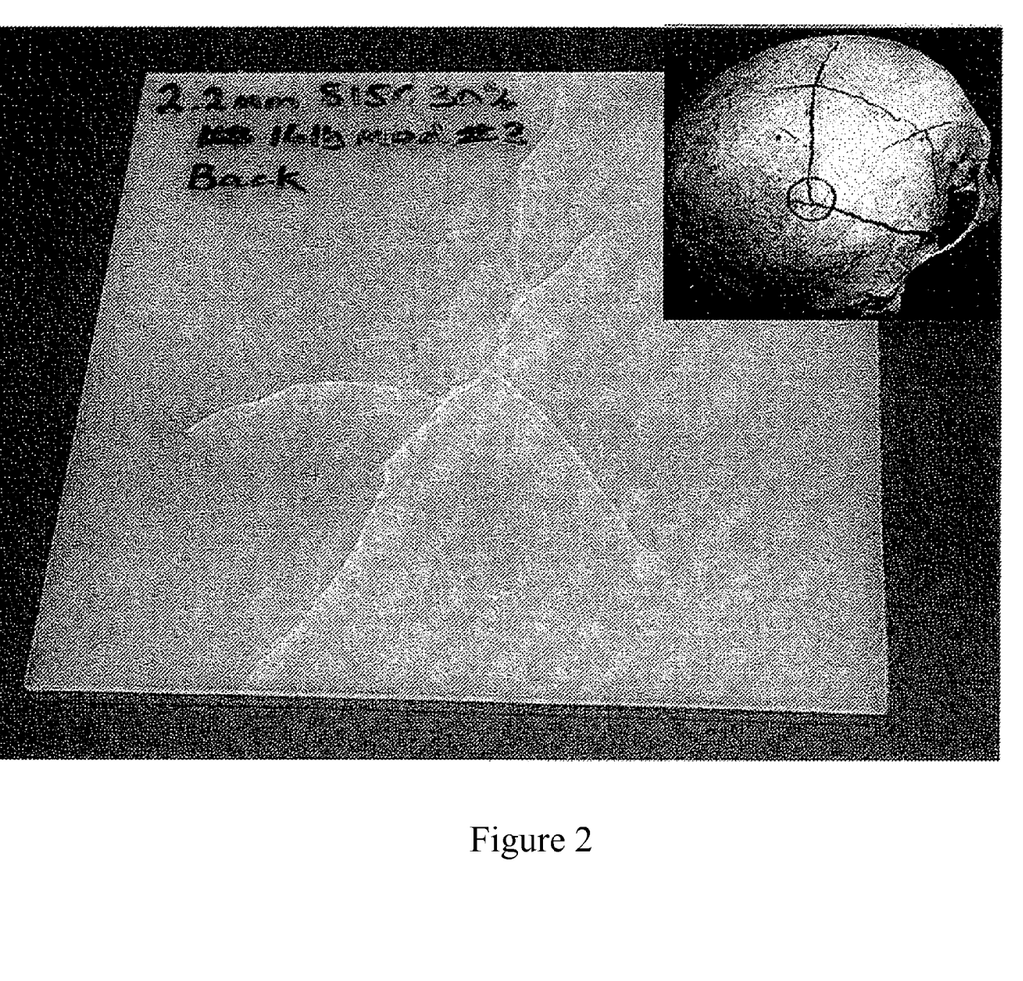
FIG. 2 shows two photographs which depict that the surrogate fracture patterns of the material shown in FIG. 1 match up well with the linear fractures from actual skull impact.

The surrogate materials were then tested in a drop tower test to establish the load to fracture conditions for different materials. The results of these tests provided the results that guided the designing of the final composition. The force to fracture of the final surrogate structures ranged from 1.4 to 1.9 kilonewtons, with an average of 1.60 kilonewtons. These values are in the same range as human cranial bone skull fracture, when the effect of skull curvature is taken into account. In addition, the resulting fracture patterns observed in the surrogate are linear, which is consistent with observations reported for impact occurring under similar loading conditions. As may be seen in the photographs in the FIG. 2, the surrogate fracture patterns match up well with the linear fractures from actual skull impact.

TABLE 1

| Material | Fracture Toughness (MPa√m) | Elastic Modulus (GPa) | Tensile Strength (MPa) | Bending Strength (MPa) |
|---|---|---|---|---|
| Tables - EPON 815C + 30% Glass Fiber | 2.74 ± 0.22 | 6.09 ± 0.56 | 53.8 ± 3.56 | N/A |
| Tables - EPON 815C + 40% Glass Fiber | 2.91 ± 0.22 | 5.95 ± 0.39 | 52.5 ± 5.30 | N/A |
| Three layer structure - EPON 815C + 30% Glass + Foam diploe | N/A | N/A | N/A | 67.3 ± 4.5 |

Thus, the surrogate multilayered material may be manufactured in a batch process or in a continuous manufacturing process. In a batch process, the precursor to the crosslinked polymer (also termed the resin) is first blended with the fibers following which it is blended with the crosslinking agent (also known as the hardener) to form a curable composition. The curable composition is placed in a mold and cured at a suitable pressure of about 0.2 MPa to about 0.8 MPa for a period of about 2 to about 6 hours. In an exemplary embodiment, the curable composition is placed in a mold and cured at a pressure of about 0.4 MPa to about 0.6 MPa for a period of about 3 to about 5 hours to produce a cured epoxy panel. The resulting surrogate multilayered material displays fracture properties and patterns that are similar to those displayed by an actual cranial bone. The surrogate multilayered material mimics the behavior of a cranial bone under dynamic blunt or penetrating impact conditions. The surrogate multilayered material has many of the properties of the human cranial bone including being structurally identical to the cranial bone. It is a three layered composite structure with the inner and outer layer having a higher fracture toughness and stiffness than the middle layer. The middle foamed layer in the surrogate multilayered material has more nearly the density and energy absorbing capacity of the middle layer in the actual cranial bone.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

While exemplary embodiments of the present invention have been described with reference to a preferred embodiment and various alternative embodiments, it will be understood by those of ordinary skill in the art that changes may be made and equivalents may be substituted for elements thereof without departing from the scope thereof. In addition, many modifications may be made to adapt a particular situation or material to the teachings of the foregoing disclosure without departing from the scope thereof. Therefore, it is intended that the invention not be limited to any particular embodiment disclosed herein, but that the invention will include all embodiments falling within the scope of the appended claims.

What is claimed is:

1. A surrogate multilayered material comprising:
a first fiber reinforced layer; the first reinforced layer comprising a crosslinked polymer and fibers;
a second fiber reinforced layer; the second reinforced layer comprising the crosslinked polymer and the fibers;
a foam layer; the foam layer disposed between the first fiber reinforced layer and the second fiber reinforced layer; where opposite faces of the foam layer are in direct contact with the first fiber reinforced layer and the second fiber reinforced layer; where the foam layer has a compressive strength of about 3.5 to about 4.5 MPa, when measured as per ASTM-D-1621-73, and a shear strength of 1.50 to about 2.15 MPa, when measured as per ASTM-C-273;
wherein the fibers in the first fiber reinforced layer and in the second fiber reinforced layer are milled fibers uniformly dispersed within the crosslinked polymer.

2. The surrogate multilayered material of claim 1, where the first fiber reinforced layer or the second fiber reinforced layer has a tensile strength of about 40 to about 130 MPa when conducted according to ASTM D 628.

3. The surrogate multilayered material of claim 1, where the first fiber reinforced layer or the second fiber reinforced layer has a fracture toughness of about 1 to about 10 MPa√m when conducted according to ASTM D 5045.

4. The surrogate multilayered material of claim 1, having a bending modulus of about 1 to about 5 MPa and a bending strength of about 60 to about 150 MPa when measured as per ASTM D 790.

5. The surrogate multilayered material of claim 1, where the crosslinked polymer is selected from the group consisting of epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, and a combination comprising at least one of the foregoing crosslinked polymers.

6. The surrogate multilayered material of claim 5, where the epoxy polymers are selected from the group consisting of diglycidyl ether of bisphenol A, diomethane diglycidyl ether, 2,2-bis(4-glycidyloxyphenyl)propane, 2,2'-((1-methylethylidene)bis(4,1-phenyleneoxymethylene))bisoxirane, 2,2-bis(4-(2,3-epoxypropyloxyl)phenyl)propane, 2,2-bis(4-hydroxyphenyl)propane, diglycidyl ether, 2,2-bis(p-glycidyloxyphenyl)propane, 4,4'-bis(2,3-epoxypropoxy)diphenyldimethylmethane, 4,4'-dihydroxydiphenyldimethylmethane diglycidyl ether, 4,4'-isopropylidenebis(1-(2,3-epoxypropoxyl)benzene), 4,4'-isopropylidenediphenol diglycidyl ether, bis(4-glycidyloxyphenyl)dimethylmethane, bis(4-hydroxyphenyl)dimethylmethane diglycidyl ether, diglycidyl ether of bisphenol F, 2-(butoxymethyl)oxirane, the reaction product of 2-(chloromethyl)oxirane and 4-[2-(4-hydroxyphenyl)propan-2-yl]phenol, modified bisphenol A-epichlorohydrin based epoxy, and a combination comprising at least one of the foregoing epoxy resins.

7. The surrogate multilayered material of claim 5, where the epoxy polymer is a diglycidyl ether of bisphenol F, having the structure shown in Formula (1):

8. The surrogate multilayered material of claim 5, where the epoxy polymer is a modified diglycidyl ether of bisphenol F and has the structure shown in Formula (2):

where n is the number of repeat units.

9. The surrogate multilayered material of claim 5, where the reaction product of 2-(chloromethyl)oxirane and 4-[2-(4-hydroxyphenyl)propan-2-yl]phenol is bisphenol A-epichlorohydrin based epoxy having the formula (3) below:

10. The surrogate multilayered material of claim 5, where the epoxy polymer has the structure of formulas (4) or (5):

11. The surrogate multilayered material of claim 5, where the epoxy polymers are cured with an amine hardener.

12. The surrogate multilayered material of claim 11, where the epoxy polymers are cured with amine hardeners selected from the group consisting of diethylene triamine, triethylenetetramine, tetraethylenepentamine, polyoxypropylenediamine, polyoxypropylenetriamine, aminoethylpiperazine, and a combination comprising at least one of the foregoing amine hardeners.

13. The surrogate multilayered material of claim 1, where the foam is a rigid open cell foam that is selected from the group consisting of polyacetal, polyolefin, polyacrylic, polycarbonate, polystyrene, polyester, polyamide, polyamideimide, polyarylate, polyarylsulfone, polyethersulfone, polyphenylene sulfide, polyvinyl chloride, polysulfone, polyimide, polyetherimide, polytetrafluoroethylene, polyetherketone, polyether etherketone, polyether ketone ketone, polybenzoxazole, polyphthalide, polyacetal, polyanhydride, polyvinyl ether, polyvinyl thioether, polyvinyl alcohol, polyvinyl ketone, polyvinyl halide, polyvinyl nitrile, polyvinyl ester, polysulfonate, polysulfide, polythioester, polysulfone, polysulfonamide, polyurea, polyphosphazene, polysilazane, polyurethane, polytetrafluoroethylene, perfluoroalkoxyethylene, polychlorotrifluoroethylene, polyvinylidene fluoride, and a combination comprising at least one of the foregoing organic polymers.

14. The surrogate multilayered material of claim 1, where the foam is a rigid open cell polyurethane foam.

15. The surrogate multilayered material of claim 1, where the fibers are organic fibers.

16. The surrogate multilayered material of claim 1, where the fibers are inorganic fibers.

17. The surrogate multilayered material of claim 1, where the fibers are glass fibers.

18. The surrogate multilayered material of claim 17, where the glass fibers are E-glass fibers.

19. The surrogate multilayered material of claim 1, with first fiber reinforced layer or the second fiber reinforced layer has a tensile strength of 53±5 MPa when measured as per ASTM D 628, a fracture toughness of 3±2 MPa when measured as per ASTM D 790, where the three layer structure having a bending strength of 68±6 MPa, when measured as per ASTM D 790.

20. The surrogate multilayered material of claim 1, where the first fiber reinforced layer and/or the second fiber reinforced layer are each crosslinked by a plurality of crosslinking agents, each of which have different activation temperatures from other activators present in the first fiber reinforced layer and/or the second fiber reinforced layer.

21. The surrogate multilayered material of claim 1, where the crosslinked polymer comprises an epoxy polymer.

* * * * *